United States Patent
Anderson

(10) Patent No.: US 8,063,774 B2
(45) Date of Patent: Nov. 22, 2011

(54) NON-TOXIC, BIODEGRADABLE SENSOR NODES FOR USE WITH A WIRELESS NETWORK

(75) Inventor: Noel Wayne Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 601 days.

(21) Appl. No.: 12/133,643

(22) Filed: Jun. 5, 2008

(65) Prior Publication Data
US 2009/0303071 A1     Dec. 10, 2009

(51) Int. Cl.
*G08B 1/08*     (2006.01)
(52) U.S. Cl. ........... 340/539.26; 340/539.28; 340/693.5; 361/752; 361/757; 702/122; 702/188
(58) Field of Classification Search .. 340/539.1–539.28, 340/870.1–870.16, 693.5, 601, 602; 324/664; 73/866.1; 701/50
See application file for complete search history.

(56) References Cited

U.S. PATENT DOCUMENTS

| | | | |
|---|---|---|---|
| 4,396,149 A * | 8/1983 | Hirsch | 239/63 |
| 5,177,660 A | 1/1993 | Kilner | |
| 5,277,997 A * | 1/1994 | Rao et al. | 429/49 |
| 5,395,707 A | 3/1995 | McCarter et al. | |
| 5,495,250 A * | 2/1996 | Ghaem et al. | 342/51 |
| RE35,257 E | 5/1996 | Reusch et al. | |
| 5,691,080 A | 11/1997 | Derzon et al. | |
| 5,718,986 A | 2/1998 | Brenner | |
| 5,916,710 A | 6/1999 | Doeff et al. | |
| 5,933,765 A | 8/1999 | Newton et al. | |
| 6,791,029 B2 * | 9/2004 | Mori et al. | 174/520 |
| 6,886,208 B2 | 5/2005 | Kemp et al. | |
| 6,975,245 B1 | 12/2005 | Slater et al. | |
| 7,003,405 B1 * | 2/2006 | Ho | 702/32 |
| 7,122,615 B1 | 10/2006 | Uhrich | |
| 7,318,010 B2 | 1/2008 | Anderson | |
| 2003/0182841 A1 * | 10/2003 | Calak et al. | 43/17.6 |
| 2006/0031490 A1 | 2/2006 | Provine et al. | |
| 2006/0080819 A1 * | 4/2006 | McAllister | 29/403.3 |
| 2007/0003885 A1 | 1/2007 | Yoshioka | |
| 2007/0039745 A1 * | 2/2007 | Anderson et al. | 172/6 |
| 2007/0082202 A1 * | 4/2007 | Yui et al. | 428/411.1 |
| 2007/0273394 A1 * | 11/2007 | Tanner et al. | 324/664 |

FOREIGN PATENT DOCUMENTS

| | | |
|---|---|---|
| WO | 0074306 A2 | 12/2000 |
| WO | 03082980 A1 | 10/2003 |
| WO | 2004089434 A1 | 10/2004 |

OTHER PUBLICATIONS

Ramani Narayan; Commercializing Technology: From Laboratory to the Marketplace—A Case Study of Starch-based Biodegradable Plastics Technology; http://www.msu.edu/user/narayan/commercializingstarchplastics.htm.
Haakko Happonen; Disposable thin and flexible power source; Enfucell SoftBattery specifications.
Mark Halper; Flat Battery: It Works On Paper; Time Magazine; http://www.tim.com/time/magazine/article/0,9171,901061211-1565509,00.html.
Peter Clarke; Paper battery developer raises $700,000; EETimes; http://www.eetimes.com/showArticle.jhtml?articleID=183702471.
Ryan Block; Enfucell's SoftBattery gets thing and flexible; Engadget; http://www.engadget.com/2006/03/27/enfucells-softbattery-gets-thin-and-flexible/.
Power Paper; Technology & Innovation; http://www.powerpaper.com/?categoryId=10625.

* cited by examiner

*Primary Examiner* — Brent Swarthout
(74) *Attorney, Agent, or Firm* — Taylor IP, P.C.

(57) ABSTRACT

A sensor node for deployment in association with an earth surface has a biodegradable plastic housing, an electronic circuit board within the housing, and at least one battery for providing electrical energy to the circuit board. The circuit board has a non-toxic substrate and at least one lead-free solder element. Each battery is a non-toxic battery.

27 Claims, 2 Drawing Sheets

NON-TOXIC, BIODEGRADABLE SENSOR NODES FOR USE WITH A WIRELESS NETWORK

FIELD OF THE INVENTION

The present invention relates to wireless networks, and, more particularly, to sensor nodes used in such wireless networks.

BACKGROUND OF THE INVENTION

Wireless sensor networks are being applied to agriculture and natural resource management. An example of a wireless network used in an agricultural application is disclosed in U.S. Patent Application Publication No. 2007/0039745 A1 (Anderson et al.), which is assigned to the Assignee of the present invention. A wireless network of this type typically includes a plurality of sensor nodes, with each sensor node having a printed circuit board connected to a battery. The circuit board and battery are typically placed within a housing. For certain applications, it may not be possible or economically feasible to retrieve the sensor nodes after the battery is depleted. Printed circuit boards used in conventional sensor nodes contain lead solder and are considered hazardous waste. Batteries may also contain environmentally unfriendly chemicals and/or materials. Thus, the widespread use of existing sensor nodes can lead to environmental damage over years of use.

SUMMARY OF THE INVENTION

The invention in one form is directed to a sensor node for deployment in association with an earth surface. The sensor node has a biodegradable plastic housing, an electronic circuit board within the housing, and at least one battery for providing electrical energy to the circuit board. The circuit board has a non-toxic substrate and at least one lead-free solder element. Each battery is a non-toxic battery.

The invention in another form is directed to a wireless network having a plurality of sensor nodes deployed in association with an earth surface. Each sensor node has a biodegradable plastic housing, an electronic circuit board within the housing, and at least one battery for providing electrical energy to the circuit board. The circuit board has a non-toxic substrate and at least one lead-free solder element. Each battery is a non-toxic battery.

DETAILED DESCRIPTION OF THE INVENTION

Figure 1:
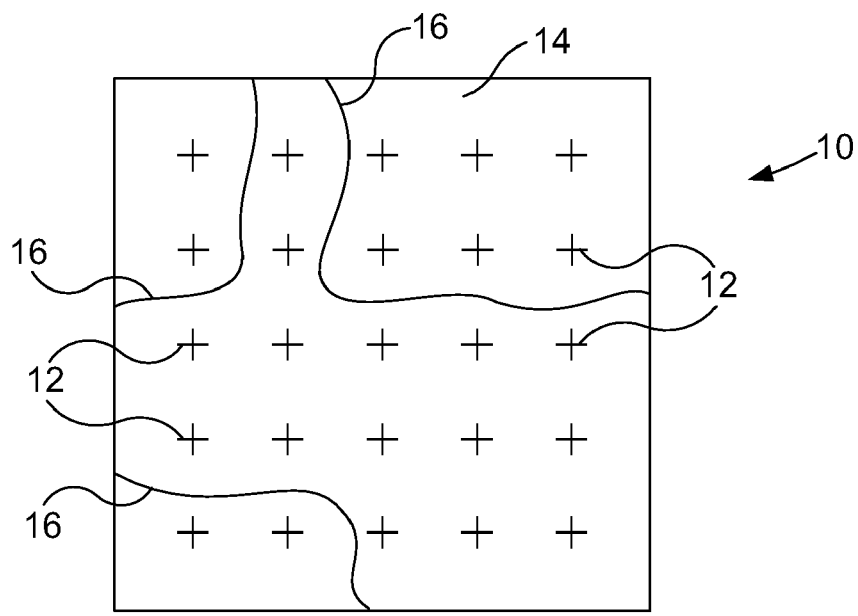
FIG. 1 is a graphical illustration of an example of a sensor node layout with respect to a geographic area overlying an earth surface.

Referring now to the drawings, and more particularly to FIG. 1, there is shown a graphical illustration of a wireless network 10 of the present invention, including an example of a sensor node layout with respect to a geographic area overlying an earth surface. Wireless network 10 can be deployed over any suitable geographic area. For example, in the embodiment illustrated in FIG. 1, wireless network 10 is assumed to be deployed in an agricultural field. As another example, wireless network 10 could be deployed for natural resource management and a geographic area could represent, e.g., a large forested area. Other applications are also possible.

Wireless network 10 includes a plurality of sensor nodes 12 (designated generally with a "+" sign) which are deployed in association with earth surface 14. Contour lines 16 are simply intended to show variances in topography, but could also represent variances in soil type, work versus non-work areas, etc. It will be appreciated that the particular layout of sensor nodes 12, such as spacing, pattern, deployment depth, etc. can vary from one application to another.

Each sensor node 12 is deployed in association with earth surface 14, broadly meaning that sensor nodes 12 could be deployed at any level within the earth surface, partially within the earth surface, or on top of the earth surface. The term "earth surface" is also broadly intended to cover any type of surface or material, such as soil, compost, sludge, manure, cellulosic materials such as stover, bagasse, wood chips, etc.

Figure 2:
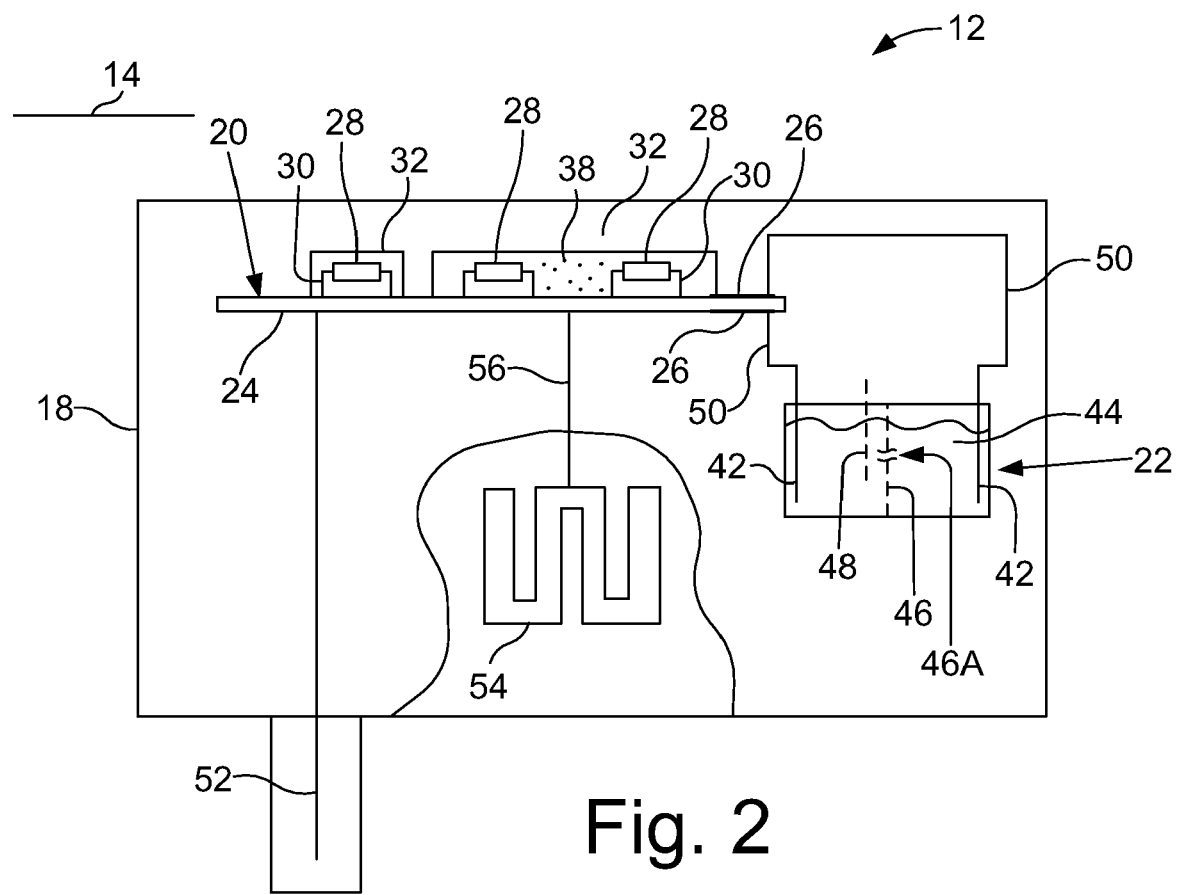
FIG. 2 is a schematic illustration of an embodiment of a sensor node of the present invention.

Referring now to FIG. 2, each sensor node 12 generally includes a biodegradable plastic housing 18, an electronic circuit board 20 within housing 18, and one or more non-toxic batteries 22.

Housing 18 is constructed from a biodegradable plastic which is selected and formed to last through the expected service life of sensor node 12. An example of a plastic of this type is made by the former Cargill Dow, LLC from corn. Other examples of biodegradable plastics include polymeric and polyester materials of many specific types. Specific examples of such plastics include a polyhydroxyalkanoate (PHA) polymer, poly(3-hydroxybutyrate) (P3HB) polyester, polyhydroxyalkanoates, poly(k-caprolactone), poly(l-lactide), and both aliphatic and aromatic polyalkylene dicarboxylic acids.

Circuit board 20 includes a non-toxic, preferably biodegradable substrate 24 and one or more lead-free solder elements 26. Substrate 24 can be formed from a suitable biodegradable material having sufficient dielectric properties. Substrate 24 can be a single layer substrate or a multi-layer substrate with solder runs between the various layers. It may be possible, e.g., to form substrate 24 from a non-hydrocarbon based plastic as described above with reference to the material types of housing 18.

Solder elements 26 are intended generally to cover any type of lead-free solder feature onboard or within circuit board 20. For example, solder elements 26 can be in the form of solder runs or solder pads carried by circuit board 20.

Circuit board 20 also includes a plurality of electronic components 28 which are carried by substrate 24. Electronic components 28 may be of any suitable type for the specific application, and can be of the surface mount (smt) type or leaded type. In the embodiment shown in FIG. 2, electronic components 28 are illustrated as including leads 30, which are preferably gold plated to prevent oxidation.

In the event that electronic components 28 are themselves not biodegradable, an encapsulation 32 may be provided around electronic components 28. Encapsulation 32 is formed from a material which is an environmentally friendly, non-degrading and durable material. For example, encapsulation 32 can be formed from glass or specific types of potting compounds. Additionally, the electronic components 28 can be encapsulated with a single encapsulation, or encapsulated for different geographic areas on circuit board 20, as shown in FIG. 2.

In one example, an electronic component 28 can be in the form of an integrated circuit (IC) formed from a non-degrading durable material such as a suitable ceramic material. The IC may include external leads which are physically held against or metallurgically bonded to solder pads on the circuit board 20, with the IC being encapsulated with a biodegradable potting material. The circuit board can of course also carry other suitable electronic components, such as an RF transceiver, etc.

Figure 3:
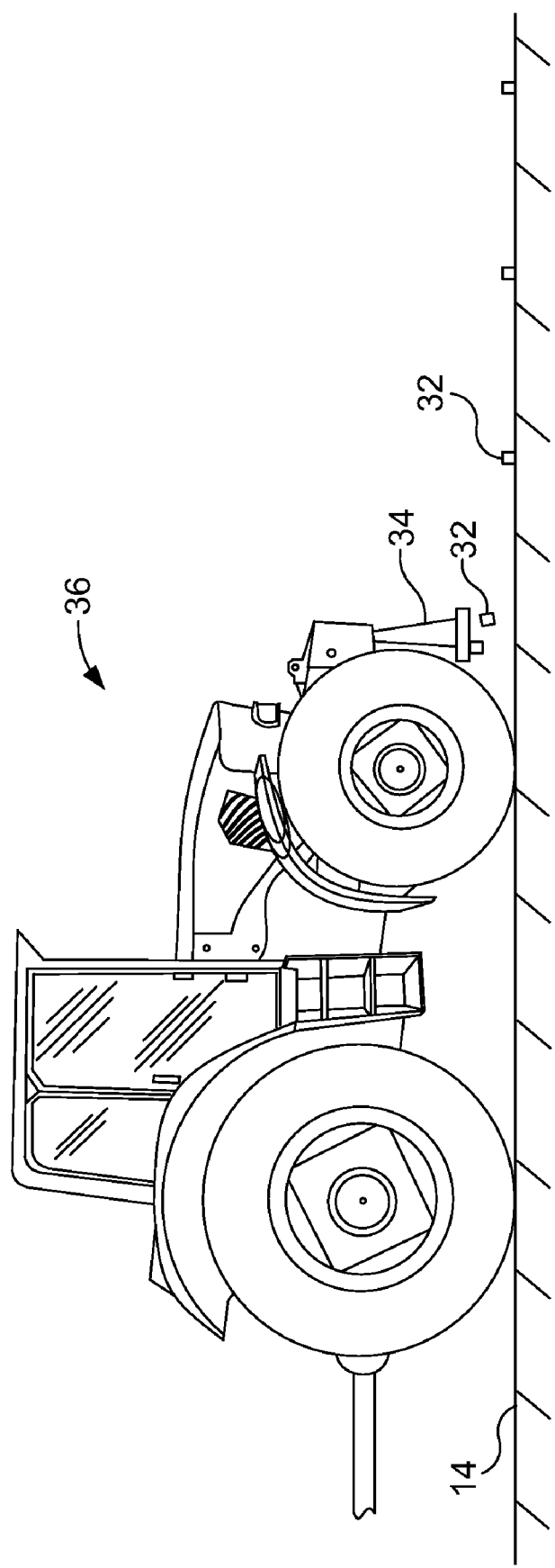
FIG. 3 is an illustration of a magnetic pick-up on a work machine which could be used to remove the non-biodegradable portions of sensor nodes from an earth surface.

Encapsulation 32 can optionally include a magnetic material which is associated therewith. In the event that the electronic components 28 are not biodegradable, the magnetic material allows the encapsulated electronic components to be removed from the earth surface using a suitable magnet. For example, referring to FIG. 3, in the case where sensor nodes 12 are deployed within an agricultural field, a strong magnet 34 carried by a tractor 36 can be used to remove each encapsulation 32 having electronic components 28 embedded therein. In the embodiment of encapsulation 32 shown in FIG. 2, magnetic particles 38 (shown in enlarged form in one of the encapsulations) are entrained within the encapsulation 32 for possible subsequent retrieval using a magnetic pick-up on a work machine or the like. It is also possible that a magnetic plate (not shown), such as a steel plate, can be affixed to the outer surface of encapsulation 32.

Battery 22 can be of any suitable configuration, such as a flexible thin film battery, etc. In the embodiment shown in FIG. 2, battery 22 generally includes a non-toxic case 40, a plurality of non-toxic electrodes 42 within case 40, and a non-toxic electrolyte 44. Case 40 is preferably also biodegradable in addition to being non-toxic, and can be formed from a biodegradable plastic as described above with reference to housing 18. Electrolyte 44 is a non-toxic, naturally originated acid such as citric acid or ascetic acid. Electrolyte 44 will thus not harm the environment upon biodegradation of case 40.

In the embodiment shown, electrolyte 44 is in contact with electrodes 42. It is also possible to provide battery 22 with an internal biodegradable membrane 46 which separates the electrolyte from at least one of the plurality of electrodes 42 (shown in dashed line as an optional feature in FIG. 2). For example, electrolyte 44 could be positioned on one side of membrane 46 and in contact with only one of the electrodes 42. Rupturing the membrane 46 (such as through an electrolyte fill hole), as shown schematically at reference 46A, for "just-in-time" use would cause electrolyte 44 to flow across case 40 to contact both electrodes 42. Alternatively, it may be possible to move the rightmost electrode 44 shown in FIG. 2 to the position shown by dashed line 48, such that both electrodes are not in contact with electrolyte 44 until membrane 46 is ruptured by a user. As yet a further example, it may be possible to place water on one side of membrane 46 and salts on the opposite side of membrane 46, wherein mixing of the water and salts occurs upon rupturing of membrane 46 to form the electrolyte.

Battery 22 may be electrically coupled with circuit board 20 using non-toxic conductors 50, such as copper or aluminum conductors. Conductors 50 may also be in the form of a conductive non-toxic ink which electrically connects between battery 22 and circuit board 20. For example, the non-toxic ink can be in the form of traces which are formed from a soy-based ink with conductive particles.

Sensor node 12 also includes a sensor 52 which is coupled with circuit board 20. Sensor 52 may be any suitable type sensor for sensing a desired parameter associated with earth surface 14, such as a temperature sensor, moisture sensor, pH sensor, etc.

Sensor node 12 further includes an antenna 54 which is affixed to housing 18 and configured for use as an antenna for wireless communications. In the embodiment illustrated in FIG. 2, antenna 54 is in the form of a conductive non-toxic ink which is printed on housing 18 and connected to at least one of the electronic components 28 onboard circuit board 20 (a portion of housing 18 is shown in fragmentary form in FIG. 2 for purposes of illustration). Antenna 54 is shown with a folded configuration but may have any suitable size and shape. Antenna 54 preferably is a patch antenna carried by housing 18, and formed from a thin sheet material, screened ink, etc. In the embodiment shown, antenna 54 is formed from a conductive non-toxic ink such as, e.g., a soy-based ink with conductive particles.

Conductor 56 interconnecting antenna 54 with one or more electronic components 28 onboard circuit board 20 may be a non-toxic conductor, such as an aluminum or copper conductor. Alternatively, conductor 56 may be a conductive non-toxic ink, such as a soy-based ink with conductive particles, as described above with reference to conductors 50.

During installation of sensor nodes 12 within wireless network 10, the sensor nodes may be manually or automatically placed in association with earth surface 14 at a desired deployment depth, spacing and pattern. The material type and configuration of the various components making up each sensor node 12 are designed with a desired service life generally corresponding to an expected service life of the one or more batteries 22. Most of the components making up each sensor node 12 are preferably biodegradable and begin the biodegradation process after depletion of the one or more batteries 22. In the event that one or more components associated with sensor node 12 are not biodegradable, such as perhaps electronic components 28, such components are designed to either be environmentally friendly or encapsulated within an encapsulation 32 to render them environmentally inert. In the event that the remaining encapsulation 32 includes or is attached to a magnetic material, the various encapsulations 32 may be picked up from the earth surface using a pick-up magnet 34 of various types and configurations.

Having described the preferred embodiment, it will become apparent that various modifications can be made without departing from the scope of the invention as defined in the accompanying claims.

The invention claimed is:

1. A sensor node for deployment in association with an earth surface, said sensor node comprising:
   a biodegradable plastic housing;
   an electronic circuit board within said housing, said circuit board having a non-toxic and biodegradable substrate and at least one lead-free solder element;
   a plurality of electronic components carried by said substrate, each said electronic component having a plurality of electrical leads;
   at least one battery for providing electrical energy to said circuit board, each said battery being a non-toxic battery; and
   a conductive non-toxic ink printed on said housing and connected to at least one of said electronic components, said conductive non-toxic ink being configured for use as an antenna for wireless communications;
   wherein all of said sensor node which is exposed to soil both upon deployment and biodegradation of said housing is at least one of non-toxic and biodegradable.

2. The sensor node of claim 1, wherein each said electronic component has a plurality of electrical leads which are gold plated.

3. The sensor node of claim 1, wherein said non-toxic ink is a soy-based ink.

4. The sensor node of claim 1, wherein said non-toxic ink has conductive particles.

5. The sensor node of claim 1, having a conductive non-toxic ink for electrical connection between each said battery, said circuit board, and an antenna.

6. The sensor node of claim 5, wherein said non-toxic ink is a soy-based ink.

7. The sensor node of claim 5, wherein said non-toxic ink has conductive particles.

8. The sensor node of claim 1, having an encapsulation around said electronic components, said encapsulation formed from a non-degrading durable material.

9. The sensor node of claim 8, wherein said encapsulation is one of a potting compound and glass.

10. The sensor node of claim 8, having a magnetic material which is one of affixed to an outer surface of said encapsulation, and embedded within said encapsulation.

11. The sensor node of claim 1, wherein each said solder element has one of a pad and a trace.

12. The sensor node of claim 1, wherein each said battery has a non-toxic case, a plurality of non-toxic electrodes within said case, and a non-toxic electrolyte.

13. The sensor node of claim 12, wherein said electrolyte is one of within said case, and separate from and installable within said case.

14. The sensor node of claim 12, wherein said electrolyte is a naturally originated acid.

15. The sensor node of claim 14, wherein said acid consists essentially of one of: citric acid and ascetic acid.

16. The sensor node of claim 12, wherein said battery has a biodegradable membrane separating said electrolyte from at least some of said plurality of electrodes.

17. The sensor node of claim 12, wherein said battery case is biodegradable.

18. A wireless network having a plurality of sensor nodes deployed in association with an earth surface, each said sensor node comprising:
- a biodegradable plastic housing;
- an electronic circuit board within said housing, said circuit board having a non-toxic and biodegradable substrate and at least one lead-free solder element;
- a plurality of electronic components carried by said substrate, each said electronic component having a plurality of electrical leads;
- at least one battery for providing electrical energy to said circuit board, each said battery being a non-toxic battery; and
- a conductive non-toxic ink printed on said housing and connected to at least one of said electronic components, said conductive non-toxic ink being configured for use as an antenna for wireless communications;

wherein all of each said sensor node which is exposed to soil both upon deployment and biodegradation of said housing is at least one of non-toxic and biodegradable.

19. The wireless network of claim 18, wherein each said electronic component has a plurality of electrical leads which are gold plated.

20. The wireless network of claim 18, having a conductive non-toxic ink for electrical connection between each said battery, said circuit board, and an antenna.

21. The wireless network of claim 18, having an encapsulation around said electronic components, said encapsulation formed from a non-degrading durable material.

22. The wireless network of claim 21, having a magnetic material which is one of affixed to an outer surface of said encapsulation, and embedded within said encapsulation.

23. The wireless network of claim 18, wherein each said battery has a non-toxic case, a plurality of non-toxic electrodes within said case, and a non-toxic electrolyte.

24. The wireless network of claim 23, wherein said battery has a biodegradable membrane separating said electrolyte from at least some of said plurality of electrodes.

25. A method of using a sensor node which is suitable for use with a wireless network, comprising the steps of:
deploying the sensor node relative to an earth surface, the sensor node having a biodegradable plastic housing, an electronic circuit board having a non-toxic substrate and at least one lead-free solder element, a plurality of electronic components carried by said substrate, each said electronic component having a plurality of electrical leads, and a non-toxic battery for providing electrical energy to the circuit board;
biodegrading at least a portion of the sensor node; and
removing a remaining portion of the sensor node from the earth surface using a magnetic pick-up;
wherein all of said sensor node which is exposed to soil both upon said deployment step and said biodegrading step is at least one of non-toxic and biodegradable.

26. The method of using a sensor node of claim 25, wherein the circuit board has a non-biodegradable encapsulation around at least one of said electronic components, and a magnetic material which is one of affixed to and embedded within said encapsulation, and wherein said removing step is carried out by magnetic attraction between said magnetic pick-up and said magnetic material.

27. The method of using a sensor node of claim 25, wherein said battery has a non-toxic case, a plurality of non-toxic electrodes within said case, a non-toxic electrolyte, and a biodegradable membrane separating said electrolyte from at least some of said plurality of electrodes, and having the step of rupturing the membrane to bring the electrolyte into contact with each of said electrodes.

* * * * *